United States Patent [19]
Roessler et al.

[11] Patent Number: 5,649,919
[45] Date of Patent: *Jul. 22, 1997

[54] ABSORBENT ARTICLE HAVING DUAL ASYMMETRIC LEG ELASTICS

[75] Inventors: Thomas Harold Roessler, Menasha; Paul Theodore Van Gompel, Hortonville; Georgia Lynn Zehner, Larsen; Daniel Robert Schlinz, Greenville; Apiromraj Srisopark, Menasha, all of Wis.

[73] Assignee: Kimberly-Clark Worldwide, Inc., Neenah, Wis.

[*] Notice: The term of this patent shall not extend beyond the expiration date of Pat. No. 5,540,672.

[21] Appl. No.: 633,387

[22] Filed: Apr. 16, 1996

Related U.S. Application Data

[62] Division of Ser. No. 259,288, Jun. 13, 1994, Pat. No. 5,540,672.

[51] Int. Cl.[6] ............................................. A61F 13/15
[52] U.S. Cl. ................................. 604/385.2; 604/373
[58] Field of Search ............................ 604/358, 378, 604/373, 385.1, 385.2

[56] References Cited

U.S. PATENT DOCUMENTS

| | | | |
|---|---|---|---|
| 3,901,236 | 8/1975 | Assarsson et al. | 128/284 |
| 4,076,663 | 2/1978 | Masuda et al. | 260/17.4 GC |
| 4,286,082 | 8/1981 | Tsubakimoto et al. | 526/240 |
| 4,430,086 | 2/1984 | Repke | 604/385 |
| 4,496,360 | 1/1985 | Joffe et al. | 604/397 |
| 4,515,595 | 5/1985 | Kievit et al. | 604/385 A |
| 4,555,244 | 11/1985 | Buell | 604/392 |
| 4,578,073 | 3/1986 | Dysart et al. | 604/397 |
| 4,585,448 | 4/1986 | Enloe | 604/378 |
| 4,586,199 | 5/1986 | Birring | 2/401 |
| 4,597,760 | 7/1986 | Buell | 604/397 |
| 4,597,761 | 7/1986 | Buell | 604/397 |

(List continued on next page.)

FOREIGN PATENT DOCUMENTS

| | | |
|---|---|---|
| 0059014A2 | 9/1982 | European Pat. Off. . |
| 0183668A2 | 6/1986 | European Pat. Off. . |
| 0217032A3 | 4/1987 | European Pat. Off. . |
| 0220950A2 | 5/1987 | European Pat. Off. . |
| 0300615A1 | 1/1989 | European Pat. Off. . |
| 0309246A1 | 3/1989 | European Pat. Off. . |
| 0391476A2 | 10/1990 | European Pat. Off. . |
| 0398392A2 | 11/1990 | European Pat. Off. . |
| 0403832A1 | 12/1990 | European Pat. Off. . |
| 0409876B1 | 1/1991 | European Pat. Off. . |
| 0487921A2 | 6/1992 | European Pat. Off. . |

(List continued on next page.)

Primary Examiner—Robert A. Clarke
Attorney, Agent, or Firm—Paul Yee

[57] ABSTRACT

An absorbent article has a lateral width, a longitudinal length, longitudinally extending side margins, a front waistband portion, a back waistband portion, and an intermediate portion which interconnects the front and back waistband portions. The article comprises a backsheet layer and an absorbent retention portion superposed on the backsheet layer. A liquid permeable topsheet layer is superposed on the retention portion to sandwich the retention portion between the topsheet layer and the backsheet layer. An elasticizing means form elasticized gathers at leg opening portions of the article. The elasticizing means include a front set of laterally opposed, longitudinally extending leg elastic members located in the article side margins in at least the intermediate portion of the article. The front elastic members are arranged asymmetrically with respect to the article length and have a selected offset toward the front waistband portion of the article. A back set of laterally opposed, longitudinally extending leg elastic members are constructed separate from the front set of elastic members and are located in the article side margins in at least the intermediate portion of the article. The back elastic members are arranged asymmetrically with respect to the article length and have a selected offset toward the back waistband portion of the article.

23 Claims, 11 Drawing Sheets

U.S. PATENT DOCUMENTS

| | | | |
|---|---|---|---|
| 4,601,717 | 7/1986 | Blevins | 604/358 A |
| 4,610,681 | 9/1986 | Strohbeen et al. | 604/396 |
| 4,626,305 | 12/1986 | Suzuki et al. | 156/164 |
| 4,642,819 | 2/1987 | Ales et al. | 2/400 |
| 4,657,539 | 4/1987 | Hasse | 604/385 A |
| 4,662,877 | 5/1987 | Williams | 604/385 A |
| 4,663,220 | 5/1987 | Wisneski et al. | 428/221 |
| 4,666,542 | 5/1987 | De Jonckheere | 156/164 |
| 4,687,477 | 8/1987 | Suzuki et al. | 604/385 A |
| 4,692,163 | 9/1987 | Widlund et al. | 604/385 A |
| 4,699,823 | 10/1987 | Kellenberger et al. | 428/219 |
| 4,704,116 | 11/1987 | Enloe | 604/385 A |
| 4,762,582 | 8/1988 | De Jonckheere | 156/164 |
| 4,808,176 | 2/1989 | Kielpikowski | 604/385.2 |
| 4,834,736 | 5/1989 | Boland et al. | 604/385.2 |
| 4,834,737 | 5/1989 | Khan | 604/385.2 |
| 4,834,738 | 5/1989 | Kielpikowski et al. | 604/385.2 |
| 4,838,969 | 6/1989 | Nomura et al. | 156/160 |
| 4,842,596 | 6/1989 | Kielpikowski et al. | 604/385.2 |
| 4,846,823 | 7/1989 | Enloe | 604/385.2 |
| 4,850,990 | 7/1989 | Huntoon et al. | 604/385.2 |
| 4,880,420 | 11/1989 | Pomparelli | 604/385.1 |
| 4,892,536 | 1/1990 | DesMarais et al. | 604/385.2 |
| 4,895,568 | 1/1990 | Enloe | 604/385.2 |
| 4,917,696 | 4/1990 | De Jonckheere | 604/385.2 |
| 4,935,021 | 6/1990 | Huffman et al. | 604/385.1 |
| 4,938,754 | 7/1990 | Mesek | 604/385.2 |
| 5,028,224 | 7/1991 | Pieper et al. | 425/80.1 |
| 5,037,415 | 8/1991 | Leroy et al. | 604/385.1 |
| 5,055,103 | 10/1991 | Nomura et al. | 604/385.2 |
| 5,092,861 | 3/1992 | Nomura et al. | 604/385.2 |
| 5,100,398 | 3/1992 | Leroy et al. | 604/385.1 |
| 5,147,487 | 9/1992 | Nomura et al. | 156/164 |
| 5,188,626 | 2/1993 | Toyoda et al. | 604/385.1 |
| 5,188,627 | 2/1993 | Igaue et al. | 604/385.2 |
| 5,226,992 | 7/1993 | Morman | 156/62.4 |
| 5,232,777 | 8/1993 | Sipinen et al. | 428/364 |
| 5,246,431 | 9/1993 | Minetola et al. | 604/385.2 |
| 5,540,672 | 7/1996 | Roessler et al. | 604/385.2 |

FOREIGN PATENT DOCUMENTS

| | | |
|---|---|---|
| 0539703A1 | 5/1993 | European Pat. Off. . |
| 0547497A3 | 6/1993 | European Pat. Off. . |
| 2078811 | 1/1982 | United Kingdom . |
| 2142241 | 1/1985 | United Kingdom . |
| 2215986 | 10/1989 | United Kingdom . |
| 2248380 | 4/1992 | United Kingdom . |
| 2251172 | 7/1992 | United Kingdom . |
| 2253131 | 9/1992 | United Kingdom . |
| 2254997 | 10/1992 | United Kingdom . |
| WO85/05254 | 12/1985 | WIPO . |
| WO92/07531 | 5/1992 | WIPO . |
| WO93/03698 | 3/1993 | WIPO . |
| WO93/05742 | 4/1993 | WIPO . |
| WO93/12746 | 7/1993 | WIPO . |
| WO93/14729 | 8/1993 | WIPO . |
| WO93/21877 | 11/1993 | WIPO . |
| WO95/07450 | 4/1994 | WIPO . |
| WO94/07451 | 4/1994 | WIPO . |

ABSORBENT ARTICLE HAVING DUAL ASYMMETRIC LEG ELASTICS

This application is a divisional of application Ser. No. 08/259,288 entitled "ABSORBENT ARTICLE HAVING DUAL ASYMMETRIC LEG ELASTICS" now U.S. Pat. No. 5,540,672 and filed in the U.S. Patent and Trademark Office on Jun. 13, 1994. The entirety of this application is hereby incorporated by reference.

FIELD OF THE INVENTION

The present invention relates to elasticized absorbent articles. More particularly, the present invention relates to absorbent articles having elasticized leg openings.

BACKGROUND OF THE INVENTION

Absorbent articles, such as disposable diapers, have included elasticized leg bands to provide elasticized gathers at the leg openings of the article. Each elasticized leg band can include various types of elastic members, such as single elastomeric strip, multiple elastomeric strips, or multiple elastomeric strands or threads arranged in separated, parallel or non-parallel configurations. The elastic members can be assembled into the article with a linear or curvilinear configuration. The curved leg elastic members can further include a reflexed curvature. Articles having the elasticized leg bands can provide improved fit and leakage protection, as compared to articles which do not include elasticized leg bands.

Conventional elasticizing systems, such as those described above, have, however, continued to exhibit shortcomings. For example, the conventional elastic systems can increase the bulk at the crotch region of the article, and can allow excessive sagging at the waistband region of the article. Conventional systems have also provided insufficient conformance to the different, varied shapes present at the front and rear of a wearer's body. As a result, there has been a continued need for improved elastic systems for the leg band regions of articles, such as disposable diapers.

BRIEF DESCRIPTION OF THE INVENTION

The present invention provides an absorbent article having a lateral width, a longitudinal length, longitudinally extending side margins, a front waistband portion, a back waistband portion, and an intermediate portion which interconnects the front and back waistband portions. The article includes a backsheet layer, and an absorbent retention portion superposed on the backsheet layer. A liquid permeable topsheet layer is superposed on the retention portion to sandwich the retention portion between the topsheet layer and the backsheet layer. An elasticizing means forms elasticized gathers at leg opening portions of the article. The elasticizing means includes a front set of laterally opposed, longitudinally extending leg elastic members located in the article side margins in at last the intermediate portion of the article. The front elastic members are arranged asymmetrically with respect to the article length and have a selected offset toward the front waistband portion of the article. A back set of laterally opposed, longitudinally extending leg elastic members is constructed separate from the front set of elastic members, and is located in the article side margins in at least the intermediate portion of the article. The back elastic members are arranged asymmetrically with respect to the article length and have a selected offset toward the back waistband portion of the article.

In their various aspects, the articles of the present invention can more closely conform to the different, natural body lines and shapes which are typically present at the front and back regions of a wearer's body. The article can also exhibit less bunching at its crotch region and can provide reduced crotch bulk. When the article is worn, the article can also exhibit less sagging at the waistband regions, and can provide improved body conformance and fit. As a result, the article can exhibit improved resistance to leakage and can provide improved aesthetics.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The structures of the present invention will be described herein in relationship to their use in disposable absorbent articles, but it should be understood that potential uses of the structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants and the like.

Figure 1:
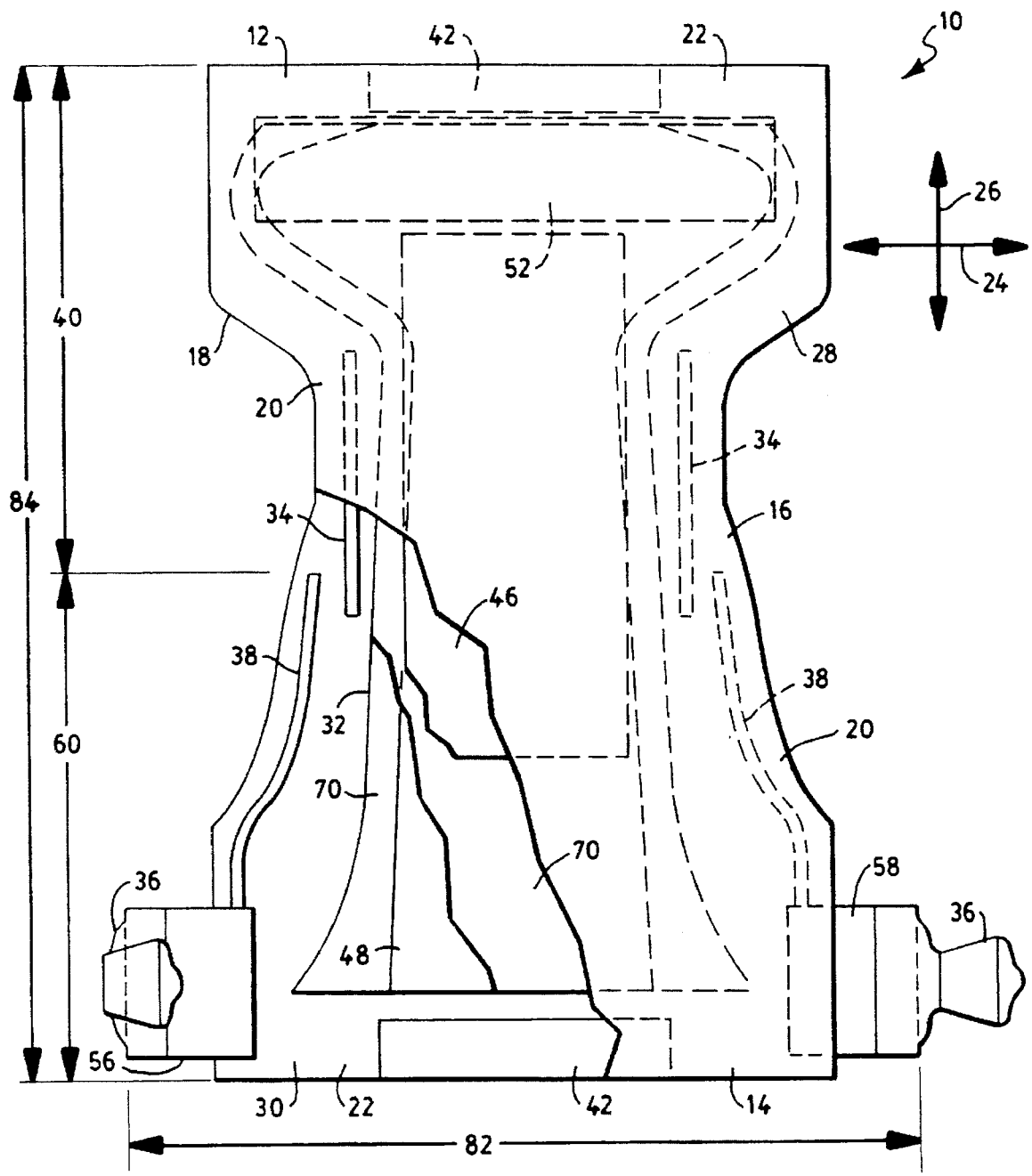
FIG. 1 representatively shows a partially cut-away, top plan view of a diaper article of the invention having spatially segmented front and back sets of leg elastic members.

With reference to FIG. 1, an absorbent article, such as diaper 10, has a lateral width 82 extending along transverse direction 24, a longitudinal length 84 extending along longitudinal direction 26, longitudinally extending side margins 20, a front waistband portion 12, a back or rear waistband portion 14, and an intermediate or crotch portion 16 which interconnects the front and back waistband portions. The article includes a backsheet layer 30, and an absorbent structure 32 which includes an absorbent retention portion 48. The absorbent retention portion is superposed on the backsheet layer 30. A liquid permeable topsheet layer 28 is superposed on the retention portion 48 to sandwich the retention portion between the topsheet layer and the backsheet layer. An elasticizing means forms elasticized gathers at leg opening portions of the article, such as diaper side margins 20. The elasticizing means includes a front set of laterally opposed, longitudinally extending leg elastic members 34 located in the article side margins in at least the intermediate portion 16 of the article. The front leg elastic members 34 are arranged asymmetrically with respect to the article length 84 and have a selected offset toward the front waistband portion 12 of the article. A back set of laterally opposed, longitudinally extending leg elastic members 38 are constructed separate from the front set of leg elastic members 34, and are located in the article side margins 20 in at least the intermediate portion 16 of the article. The back leg elastic members are arranged asymmetrically with respect to the article length 84, and have a selected offset toward the back waistband portion 14 of the article.

FIG. 1 is a representative plan view of diaper 10 of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. In the shown embodiment, diaper 10 has a front waistband region 12, a back waistband region 14, an intermediate crotch region 16 which interconnects the front and rear waistband regions. The outer edges of the diaper define a periphery 18 in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear. The diaper additionally has a transversely extending, lateral width dimension 24 and a longitudinal, length dimension 26.

Diaper 10 typically includes a porous, liquid permeable topsheet 28; a substantially liquid impermeable backsheet 30; an absorbent structure 32, positioned between the topsheet and backsheet; a surge management portion 46; and elastic members, such as leg elastics 34 and 38 and waist elastics 42. The surge management portion is positioned in liquid communication with the absorbent structure, and the absorbent structure includes a retention portion 48. Topsheet 28, backsheet 30, absorbent structure 32, surge management portion 46 and the elastic members 34, 38 and 42 may be assembled in a variety of well-known diaper configurations. In addition, the diaper can include a system of containment flaps 62, and can include a system of side panel members 56 and 58.

As representatively shown, topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery 18 of diaper 10. The periphery delimits the outer perimeter of the diaper 10, and in the illustrated embodiment, comprises laterally extending marginal end edges 22, and contoured longitudinally extending marginal side edges 20. The diaper 10 has front and back waistband regions 12 and 14, respectively, extending from the laterally extending end edges 22 of diaper periphery 18 toward the transverse center line of the diaper along a distance of from about 2 percent to about 10 percent of the overall length of diaper 10. The waistband regions comprise those upper portions of diaper 10, which when worn, wholly or partially cover or encircle the waist or mid-lower torso of the wearer. The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge typically occur in the diaper or other disposable absorbent article.

Topsheet 28 presents a body-facing surface which is compliant, soft-feeling, and non-irritating to the wearer's skin. Further, topsheet 28 can be less hydrophilic than retention portion 48, and is sufficiently porous to be liquid permeable, permitting liquid to penetrate through its thickness. The topsheet layer has marginal side regions, and has marginal end regions.

A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant, such as about 0.28% Triton X-102 surfactant. The surfactant can be applied by any conventional means, such as spraying, printing, brush coating or the like.

The surfactant material, such as a conventional wetting agent, can be applied to a medial section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips employed to secure the containment flaps 62 onto topsheet 28 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10.

In particular embodiments of the invention, backsheet 30 is a polyethylene film having a thickness of from about 0.012 millimeters (0.5 mil) to about 0.051 millimeters (2.0 mils). In the shown embodiment, the backsheet is a film having a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. Backsheet 30 typically provides the outer cover of the article. Optionally, however, the article may comprise a separate outer cover member which is in addition to the backsheet.

Backsheet 30 may optionally be composed of a microporous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise be provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch), to provide side margins. Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

It should be readily appreciated that the above-described attachment means may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the attached marginal regions of topsheet 28 can include marginal end regions. The attached marginal end regions are located longitudinally outboard of the end edge regions of the retention portion 48 and/or surge management portion 46. Similarly, the attached marginal regions of backsheet 30 can include attached marginal end regions, which can be located longitudinally outboard of the end edge regions of the retention portion and/or surge management portion.

An absorbent body, such as absorbent structure 32, is positioned between topsheet 28 and backsheet 30 to form diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

Figure 2:
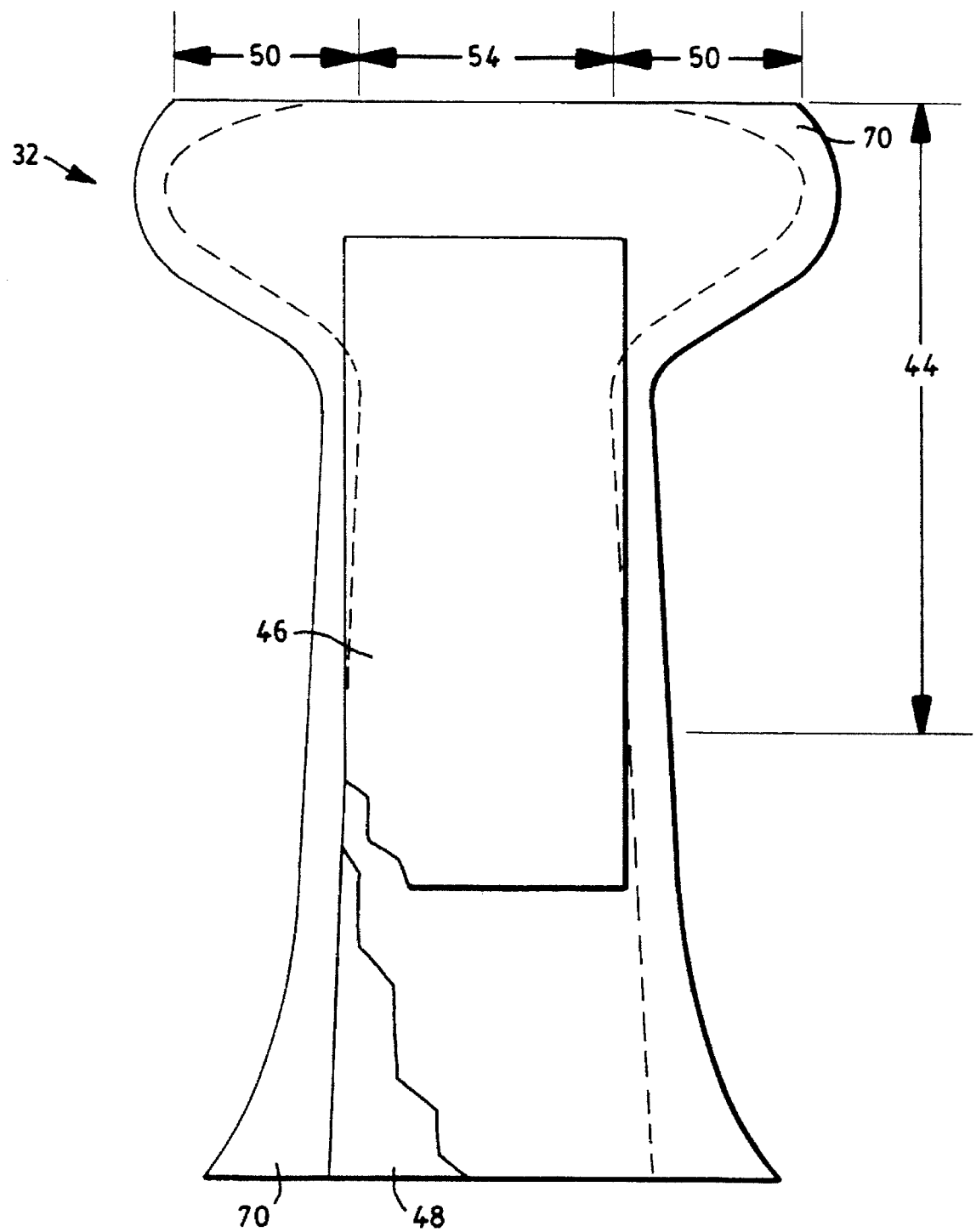
FIG. 2 representatively shows an absorbent structure which can be employed in the present invention.

With reference to FIG. 2, absorbent structure 32 can include a liquid-acquisition, target zone 44, and has a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions 50 and a central region 54. Target zone 44 encompasses the area where repeated liquid surges typically occur in absorbent structure 32. The particular location where liquid is discharged, such as during urination, can vary depending on the age and gender of the wearer. For example, male infants tend to urinate further toward the front end of the diaper. The female target zone is located closer to the center of the crotch. As a result, the shape and relative longitudinal placement of surge management portion 46 can be selected to best correspond with the actual target zone of either or both categories of wearers. Generally stated, the target zone is a section of absorbent structure 32 which is located in the front 60% of the length of the absorbent structure. With reference to the percentage of the total length of absorbent structure 32 measured into the absorbent structure from the front waistband edge thereof, the target zone may preferably comprise a region which begins at a line positioned approximately 10% of the absorbent structure length away from the front waistband edge and ends at approximately 60% of the absorbent structure length away from the front waistband edge.

The ear regions comprise portions which generally extend inwardly from the outermost lateral side edges of the absorbent structure toward its longitudinal center line. Thus, when the diaper is worn, the ear regions are configured to generally engage the sides of the wearer's waist and torso, and central region is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In a particular aspect of the invention, the absorbent structure has an absorbent capacity of at least about 200 gm of synthetic urine. Alternatively, the absorbent structure can have an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

Retention portion 48 can, for example, comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent (not contradictory) with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/ smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled "ABSORBENT COMPOSITES AND ABSORBENT ARTICLES CONTAINING SAME" and filed on Sep. 11, 1991 (Attorney Docket No. 10174), the disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. patent application Ser. No. 184,302 of S. Kellenberger and entitled "ABSORBENT PRODUCTS CONTAINING HYDROGELS WITH ABILITY TO SWELL AGAINST PRESSURE" (Attorney Docket No. 8786); European Patent Application EP 0 339 461 A1, published Nov. 2, 1989; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desireable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desireable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–14 grams of fluff and more preferably includes about 10–12 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8.5 grams of superabsorbent polymer. Sufficient superabsorbent polymer is incorporated into retention portion 48 to provide an adequate total absorbent capacity of at least about 300 gm of urine. For example, a medium size diaper for an infant weighing about 13–23 lb can typically have a total retention capacity of about 500 grams of urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled "METHOD AND APPARATUS FOR INTERMITTENTLY DEPOSITING PARTICULATE MATERIAL IN A SUBSTRATE" and issued Jul. 2, 1991 (Attorney Docket No. 8761), the disclosure of which is hereby incorporated by reference in a manner that is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches, the narrowest portion of the crotch section has a width of about 3.5 inches and the back waistband region has a width of about 4.5 inches.

The entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

At least the bodyside layer of wrap sheet 70 has a pore distribution wherein no more than about 5 percent of the pores, as measured by Coulter porometry, are greater than about 50 micrometers in diameter. For example, the complete wrap sheet 70, or at least the bodyside layer of the wrap sheet, may comprise a meltblown web composed of meltblown polypropylene fibers having a fiber size of about 5 micrometers and arranged to form a basis weight within the range of about 8–20 gsm.

Another example of absorbent wrap 70 may comprise a low porosity cellulosic tissue web composed of an approximately 50/50 blend of hardwood/softwood fibers. The tissue has a 13 lb basis weight at the reel and a porosity of about 90 cfs/sq. ft. Similar to the meltblown wrap sheet material, the entire tissue wrapsheet material, or at least the bodyside layer thereof, has not more than about 5 percent of its pores greater than about 50 micrometers in diameter. Preferably, not more than about 1 percent of the pores are greater than 50 micrometers in diameter.

Absorbent wrap 70 may comprise a multi-element wrapsheet which includes a separate bodyside wrap layer and a separate outerside wrap layer, each of which extends past all or some of the peripheral edges of retention portion 48, as representatively shown in FIGS. 1 and 2. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, the bodyside and outerside layers of absorbent wrap 70 extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

To provide the bonding between the bodyside and outerside portions of absorbent wrap 70, an adhesive, such as National Starch 72-3723 adhesive, can be printed onto the appointed bonding areas of the absorbent wrap with, for example, a rotogravure-type system. The adhesive is available from National Starch and Chemical Co., a business having offices in Bridgewater, N.J., and rotogravure-type adhesive applicators are available from Egan Machinery Division, a business having offices at Oconto Falls, Wis. Retention portion 48 can then be placed between the bodyside and outerside portions of absorbent wrap 70, and the mating edges of the absorbent wrap portions can be bonded together to provide a generally complete peripheral seal along substantially the entire perimeter of the retention portion 48. In the illustrated embodiment, the adhesive is applied at an add-on rate of about 5 grams of solids per square meter of bonding to attach together the lapping edges of the bodyside and outerside portions of absorbent wrap 70.

With alternative arrangements having an absorbent wrap composed of a nonwoven meltblown fibrous web, the peripheral sealing of the bodyside and outerside wrap layers may be accomplished by employing conventional techniques, such as hot calendering, ultrasonic bonding or the like, to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point and release the liquid to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

Surge management portion 46 can have a generally uniform thickness and cross-sectional area. Alternatively, a configuration can be used wherein the bodyside surface area of the surge management portion is greater or less than the surface area of a section taken along an X-Y plane located below the bodyside surface of the surge management portion.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

In the various embodiments of the invention, at least a major part of surge management portion 46 is located within target zone 44, and optionally, the surge management portion can have an areal extent which extends completely over target zone 44. Retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in target zone 44, however, the particles can cause the structure to retain and hold unacceptably high amounts of the liquid. In addition, the transport of liquids away from target zone 44 to other sections of absorbent structure 32, particularly retention portion 48, can be undesirably impaired.

As mentioned previously, surge layer 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in a generally sideways (X-Y) direction.

A capillary force differential created at the interface between the retention portion 48 and the material immediately adjacent the bodyside of the retention portion can improve the containment characteristics of absorbent structure 32. For example, if the surge management portion is composed of layer 46 positioned immediately adjacent to the retention portion, and if the surge layer is appropriately configured to provide and maintain a relatively lower capillary attraction, as compared to the capillary attraction exhibited by retention portion 48, then liquid surges occurring in target zone 44 tend to be desorbed more readily from the surge management portion and into the retention portion. Because retention portion 48 can thereby have a relatively higher capillarity than surge management portion 46, the liquid surges tend to be drawn into retention portion 48 and distributed to the more remote regions thereof by wicking along the plane generally defined by the retention portion.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately entered about the longitudinal center line of absorbent structure 32, and positioned primarily in a central region of the front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance from a front waistband end edge of the retention portion 48.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

In particular configurations of the invention, the surge material can include bicomponent fibers. For example, polypropylene/polyethylene bicomponent fibers may be employed to form the bicomponent fiber portion of any of the described fabrics. In addition, the bicomponent fibers may be flat crimped or helically crimped.

In particular aspects of the invention, the fibrous nonwoven web comprising surge management portion 46 can be a bonded, uniformly mixed, single layer structure having a basis weight of at least 20 grams per square meter, a void volume between about 40 and 60 cubic centimeters per gram of web at a pressure of 689 dynes per square meter (0.01 psi), a permeability of about 5,000 to about 8,000 darcy, a porosity of about 97.2% to about 98.8% and a surface area per void volume of about 24 to about 49 square centimeters per cubic centimeters. The web fibers may be thermoplastic, and may be heat bonded to one another. In addition, the web structure can have a density within a range of about 0.017–0.025 gm/cc, as determined at a pressure of 689 dynes per square meter (0.01 psi).

For example, the surge management portion may include a substantially homogeneous single-layer fibrous nonwoven web having a basis weight of about 48.8 gsm created by using about 40 percent by weight of a Hoechst Celanese type 295 6.0-denier polyester fibers and 60 percent by weight of a BASF 3.0-denier polyethylene sheath/polyester core bicomponent fibers. The homogeneous blend of fibers were bonded together using hot air passed through the web mass at a temperature of 135° C. for approximately 4 seconds. The resultant web exhibited a void volume of about 52 cc/gm, a SA/VV value of about 29.9 cm$^2$/cc, a porosity of about 98.5%, a permeability of about 6925 darcy, a saturation capacity of about 44 gm/gm, a wet compression resilience of about 81%, and a dry compression resilience of about 86%.

The basis weight of surge portion 46 can be important for providing a total holding capacity which is adequate to temporarily retain the amount of liquid that is typically discharged by a wearer during a single surge/insult of liquid into the absorbent article. It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends. The surge management material employed with the present invention will be at least about 20 grams per square meter with no real upper limit, with the target range being from about 40 to about 68 grams per square meter.

To ensure rapid intake of liquid, the overall structure of the surge portion 46 should have hydrophilic tendencies. At least a portion of the fibers should have a contact angle less than 90 degrees. As a result, the fibrous nonwoven web will have sufficient hydrophilic tendencies when the web has a saturation capacity greater than 55 grams of 0.9% saline solution per gram of web.

Another important feature of the surge material employed with the present invention is its resiliency in both the wet and dry states. A unique feature of the surge material is the amount of liquid which the material is able to absorb upon rapid insult. In addition, once the liquid has been absorbed, the surge material does not readily collapse. Excessive collapse would be detrimental to the overall performance of the material in that the collapsing of the material would result in a reduced capacity for retaining liquid. Surge materials employed with the present invention should have compression resilience values in both the wet and dry states of at least about 60%.

The distinctive permeability, specific volume, porosity, and ratio of surface area to void volume parameters within the surge management portion of the invention can advantageously provide for a sufficiently rapid uptake of the liquid surges delivered onto the target zone, and also allow a controlled spreading of the liquid through the void volume of its structure to temporarily fill it. Over a relatively short period of time, the surge management portion can then be substantially completely desorbed through the cooperative operation of the underlying or otherwise adjacent liquid retention portion.

The surge management portion is configured to cooperate with the other diaper components, such as top sheet 28 and retention portion 48, to provide for a rapid uptake of liquid discharges from the wearer. It is appreciated that a surge material with relatively small pore sizes may exhibit a rate of liquid penetration into the retention portion which may be too slow. A layer of surge management material having relatively large pore sizes, however, may provide insufficient restriction to sideways movement of liquid through the material along the plane of the material layer. As a result, the liquid may run off to the sides of the layer and leak from the article before the absorbent retention material can gather and contain the liquid. Such undesired, excessive run off may become more apparent when the absorbent material has already absorbed one or more previous discharges of liquid.

To help reduce the occurrence of excessive run off, the surge management portion of the present invention can be configured to have edge barriers constructed along selected edge regions thereof. In particular aspects, the edge barriers can be provided for by separate layers of barrier material or by edge regions which are otherwise configured to include relatively small pores therein. The small pore regions can be located along the end edge regions and/or side edge regions of the surge management portion, and are configured to be sufficiently continuous to provide operable barriers to the sideways movement of liquid.

In the various configurations of the invention, the edge barrier may be provided at only the longitudinally spaced, laterally extending end edges of the surge material. Alternatively, the edge barrier may be provided at only the laterally spaced, longitudinally extending side edges of the surge material, and optionally may be provided at both the end and side edges of the surge material to provide desire performance.

Leg elastic members 34 and 38 are disposed adjacent the periphery 18 of diaper 10 along each of the longitudinal side edges 20. The leg elastic members 34 and 38 can be connected to either or both of the topsheet and backsheet layers to provide elasticized side margins of the diaper article, and can be arranged to draw and hold diaper 10 against the legs of the wearer. Waist elastic members 42 may also be disposed adjacent either or both of the end edges of diaper 10 to provide elasticized waistbands.

Elastic members 34, 38 and 42 are typically secured to diaper 10 in an elastically contractible condition so that in a normal, under-strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other means, such as heat-shrink elastic material, may be used to gather the garment.

In the embodiment illustrated in FIG. 1, leg elastic members 34 and 38, in combination, extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34, 38 and 42 may have any of a multitude of configurations. For example, the width of the individual elastic members 34, 38, and 42 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt or other type of adhesive.

In particular configurations of the invention, for example, leg elastic members 34 and/or 38 may comprise a carrier sheet to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer available from DuPont, a business having offices in Wilmington, Del. Each elastic strand is typically within the range of about 420–1050 decitex (dtx), and preferably, is about 940 dtx in an embodiment of the invention wherein three strands are employed for each elasticized legband. In addition, leg elastics 34, 38 may be generally straight or optionally curved. For example, the curved elastics can be inwardly bowed toward the longitudinal centerline of the diaper (inwardly convex) with the innermost point (or apex, relative to the cross-direction of the article) of the set of curved elastic strands positioned relatively inward from the outer most edge of the set of elastic strands. In particular arrangements, the curvature of the elastics may or may not be configured or positioned symmetrically relative to the lateral centerline of the diaper. As representatively shown in FIG. 1, the curved elastics may have an inwardly bowed and outwardly bowed, reflex-type of curvature, and the lengthwise center of an individual elastic member may be offset by a selected distance toward either the front or rear waistband of the diaper to provide desired fit and appearance.

The distinctive elasticizing means of the invention can advantageously be configured to form elasticized gathers at the leg opening portions located along at least a portion of the lateral side margins 20 of the article. More particularly, the elasticizing means can include a front set of laterally opposed, longitudinally extending leg elastic members 34 located in the article side margins in at least the intermediate portion of the article. The front leg elastic members are arranged asymmetrically with respect to the article length. Each of the front elastic members 34 starts in the crotch region 16 of the diaper and extends toward the front waistband region 12. A back set of laterally opposed, longitudinally extending leg elastic members 38 are configured spatially separated from the front set of elastic members, and are located in the article side margins in at least the intermediate portion of the article. The back elastic members are arranged asymmetrically with respect to the article length. Each of the back leg elastic members 38 starts in the crotch region 16 of the diaper and extends toward the back waistband region 14. One or more of the front and back leg elastic members can include a plurality of separate, generally longitudinally extending, elastomeric strands.

Figure 6:
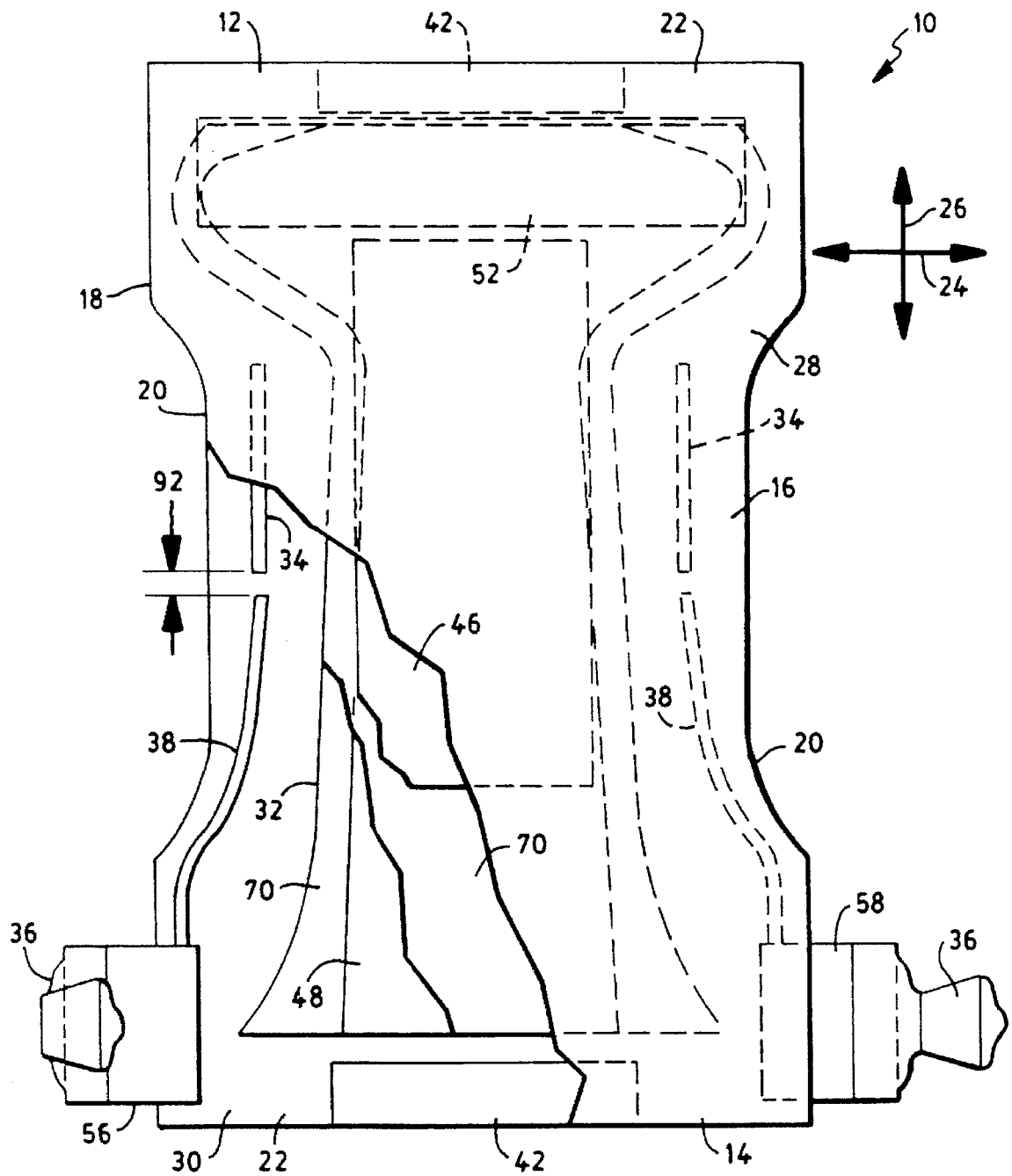
FIG. 6 representatively shows a partially cut-away, top plan view of an article of the invention having a set of substantially straight front leg elastic members and a set of curvilinear back leg elastic members which are longitudinally separated from the front leg elastics by a selected gap distance.

As representatively shown in FIG. 6, particular aspects of the invention can include a substantially straight, front leg elastic member 34 which has one of its terminal ends longitudinally spaced from a terminal end of its correspondingly associated and cooperating back leg elastic member 38 by a selected distance 92. In the illustrated embodiment, for example, the corresponding terminal ends of each cooperating pair of front and back leg elastics are located in the crotch section 16 of the diaper, and the back leg elastics are curvilinear and shaped as mirror-images of each other. The longitudinal spacing distance 92 can be at least about 0.5 cm. Alternatively, the longitudinal spacing distance can be at least about 1 cm, and optionally is at least about 5 cm. In other aspects of the invention, the longitudinal spacing distance 92 between the front and back leg elastic members is not more than about 20 cm. Alternatively, the longitudinal spacing distance 92 is not more than about 15 cm and optionally is not more than about 10 cm to provide desired performance. The front leg elastics are constructed to provide better fit at the legs in the front section of the diaper, and the curved, outwardly flared back leg elastics can provide improved fit about the buttocks of the wearer.

Figure 3:
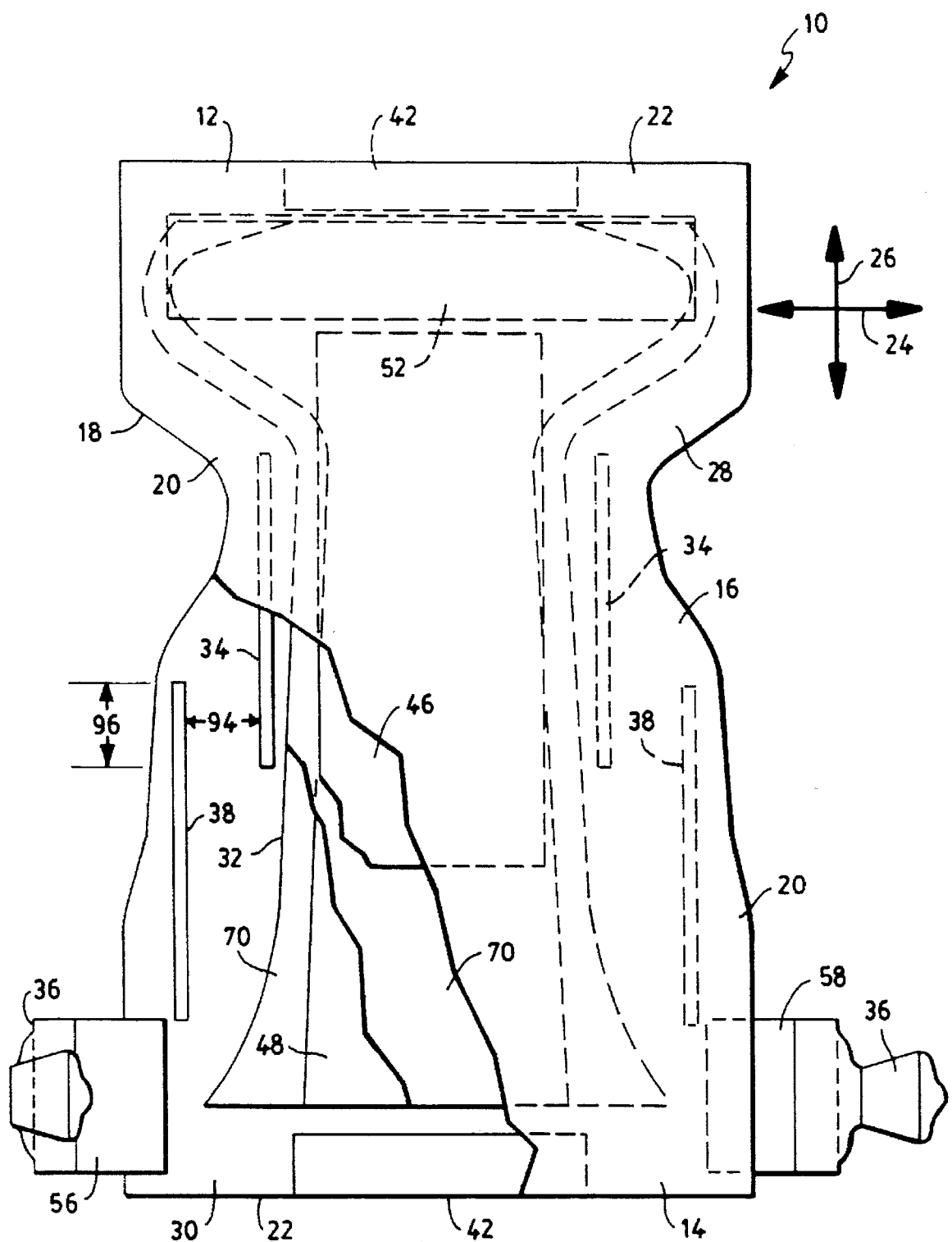
FIG. 3 representatively shows a partially cut-away, top plan view of an article having a set of front elastic members which are laterally spaced with respect to a back set of leg elastic members.

With reference to FIG. 3, each front leg elastic member 34 can be laterally spaced from its correspondingly associated and cooperating back leg elastic member 38 by a selected lateral spacing distance 94. In particular aspects of the invention, lateral spacing distance 94 can be not less than about 0.5 cm. Alternatively, the lateral spacing distance 94 can be not less than about 1 cm, and optionally, can be not less than about 5 cm. In other aspects of the invention, the lateral spacing distance 94 between the corresponding front and back leg elastic members can be not more than about 20 cm. Alternatively, the lateral spacing distance 94 can be not more than about 15 cm, and optionally, can be not more than about 10 cm to provide desired performance.

The various aspects of the invention can also be configured to have an end portion of each front leg elastic member 34 arranged in a longitudinally overlapping relation with respect to a selected end portion of its correspondingly associated and cooperating back leg elastic member 38. As illustrated in FIG. 3, each front leg elastic member can be arranged substantially parallel to its associated back leg elastic member along the region of overlap. Alternatively, each front leg elastic member 34 can be arranged substantially non-parallel to its associated back leg elastic member 38 along the region of overlap. In the resultant configurations, the corresponding front and back leg elastics are mutually partially-overlapping. The front leg elastic member partially overlaps its corresponding back leg elastic member, and the back leg elastic member partially overlaps its corresponding front leg elastic member.

In particular aspects of the invention, an overlap distance 96 between corresponding front and back leg elastic members is at least about 0.5 cm. Alternatively, the overlap distance 96 is at least about 1 cm, and optionally, is at least about 2 cm to provide desired benefits.

In other aspects of the invention, the overlap distance 96 with respect to corresponding front and back leg elastic members is not more than about 25 cm. Alternatively, the overlap distance 96 can be not more than about 10 cm, and optionally, can be not more than about 5 cm to provide improved performance.

The various aspects of the invention can have a configuration wherein at least about 55 percent of either or both of the front leg elastic members 34 are located in a front half section 40 (FIG. 1) of the article. Alternatively, at least about 75 percent of the front leg elastic members are located in the article front half section 40, and optionally, at least about 90 percent of the front leg elastic members are located in the article front half section.

In further aspects of the invention, one or more of the back leg elastic members 38 can be arranged with at least about 55 percent of the back leg elastic member located in a back half section 60 (FIG. 1) of the article. Alternatively, at least about 75 percent of the back leg elastic members 38 is located in the article back half section 60, and optionally, at least about 90 percent of the back leg elastic member is located in the article back half section.

Figure 4:
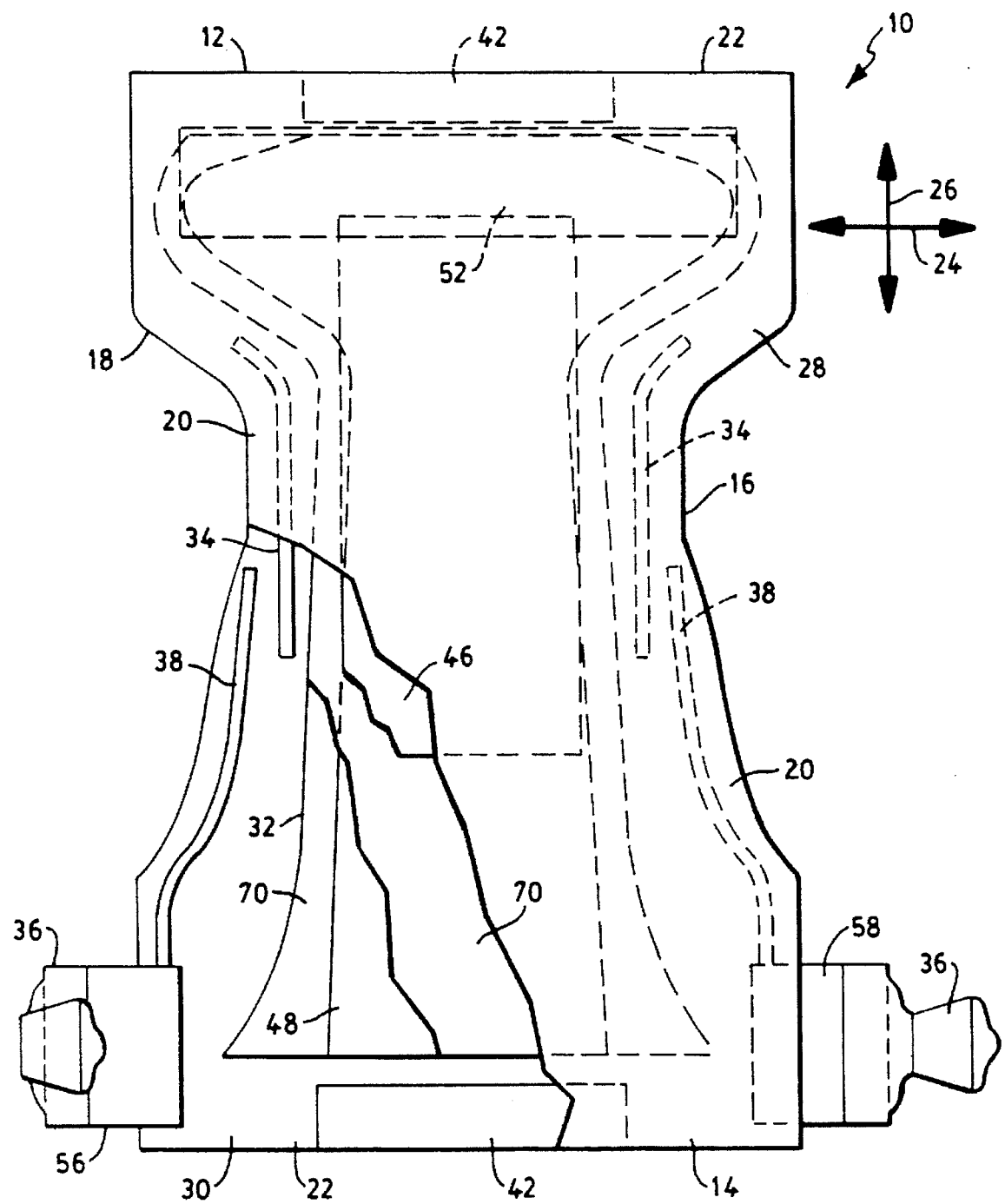
FIG. 4 representatively shows a partially cut-away, top plan view of an article of the invention having curvilinear front leg elastic members laterally spaced from curvilinear back leg elastic members, wherein the front elastic members are in a longitudinally overlapping relation with respect to a selected portion of the back leg elastic members.
Figure 5:
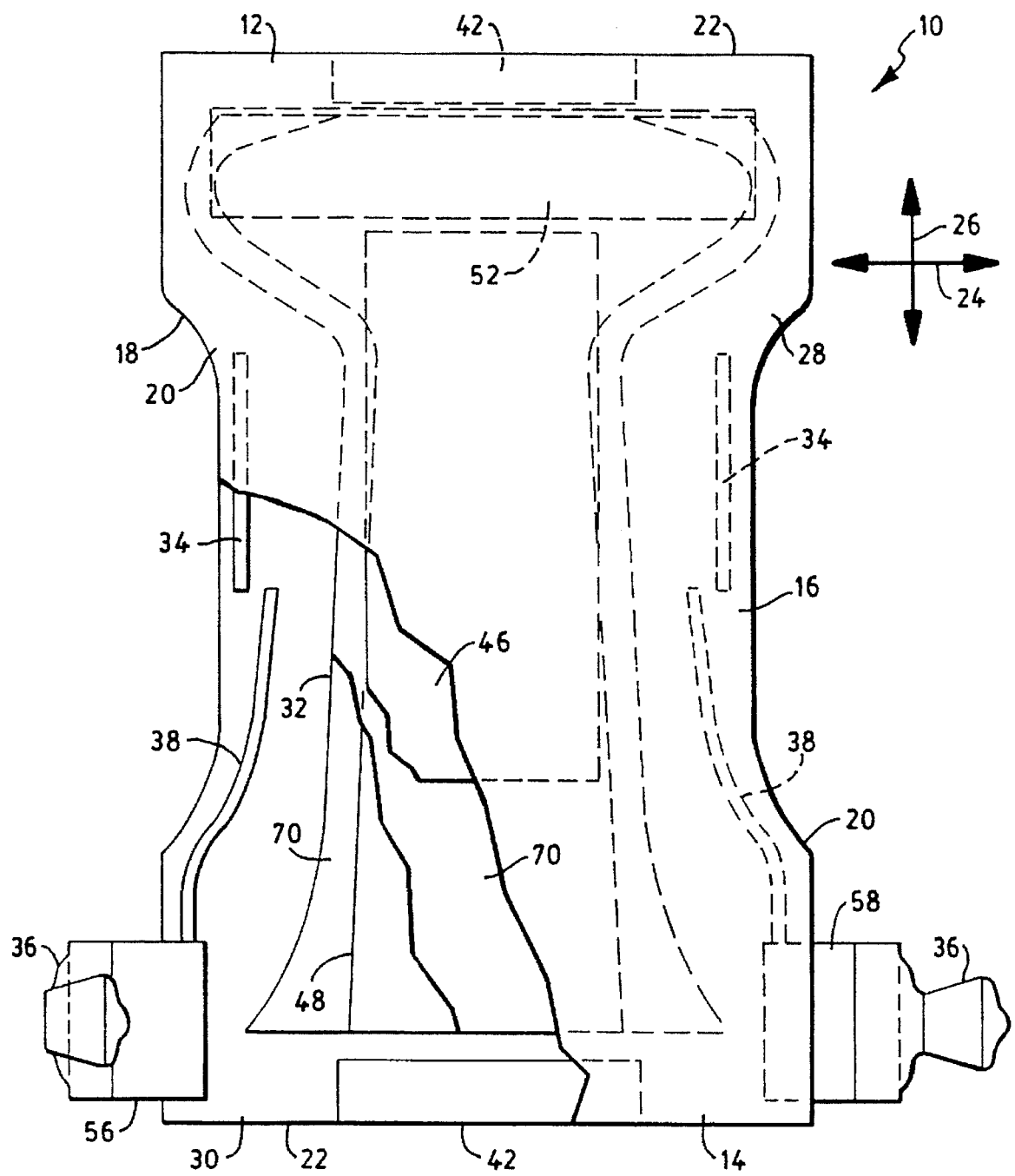
FIG. 5 representatively shows a partially cut-away, top plan view of an article of the invention having a set of back leg elastic members arranged in a curvilinear configuration.

With reference to FIG. 3, the various configurations of the invention can include front leg elastic members 34 and back leg elastic members 38 which are substantially linear and straight. In particular configurations of the invention, the back leg elastic members 38 can have a curvilinear configuration (FIG. 1). In other arrangements of the invention, front leg elastic members 34 can have a curvilinear configuration. In still further constructions of the invention, the front leg elastic members 34 and the back leg elastic members 38 can both have a curvilinear arrangement (FIG. 4).

Figure 7:
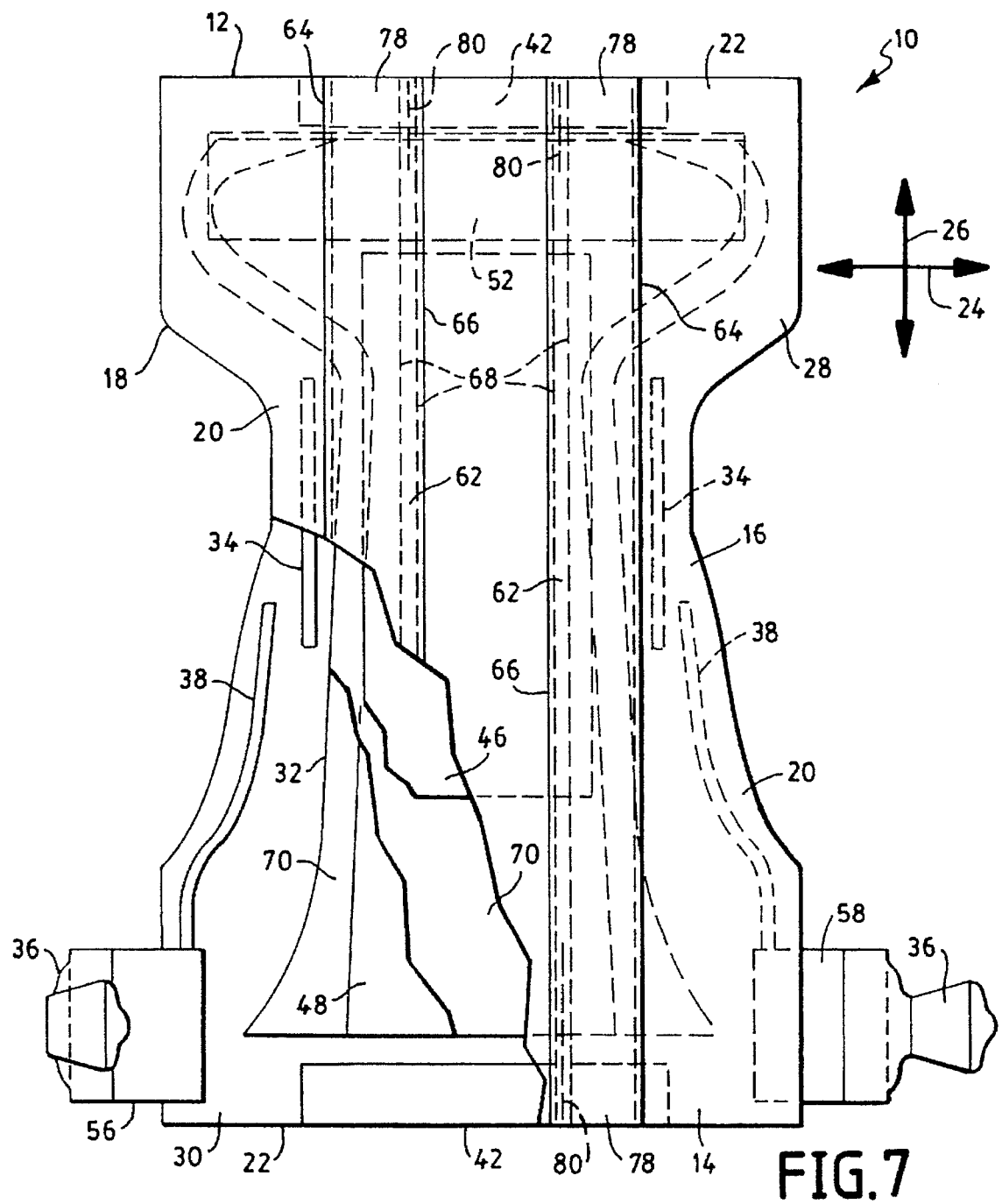
FIG. 7 representatively shows a partially cut-away, top plan view of an article of the invention having a set of containment flaps which are attached to the article at a location which is laterally inboard from the front and back leg elastic members.
Figure 8:
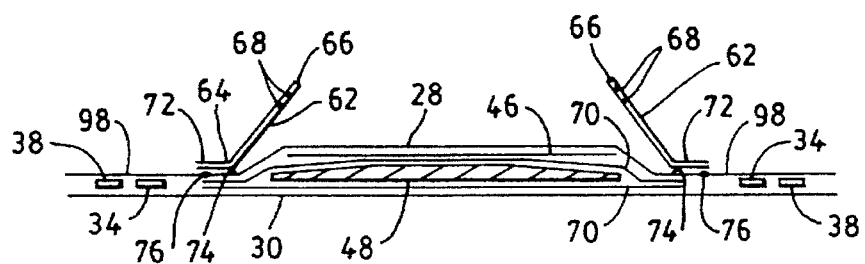
FIG. 8 representatively shows a schematic, expanded, cross-sectional view taken along Section 8—8 of FIG. 7.
Figure 9:
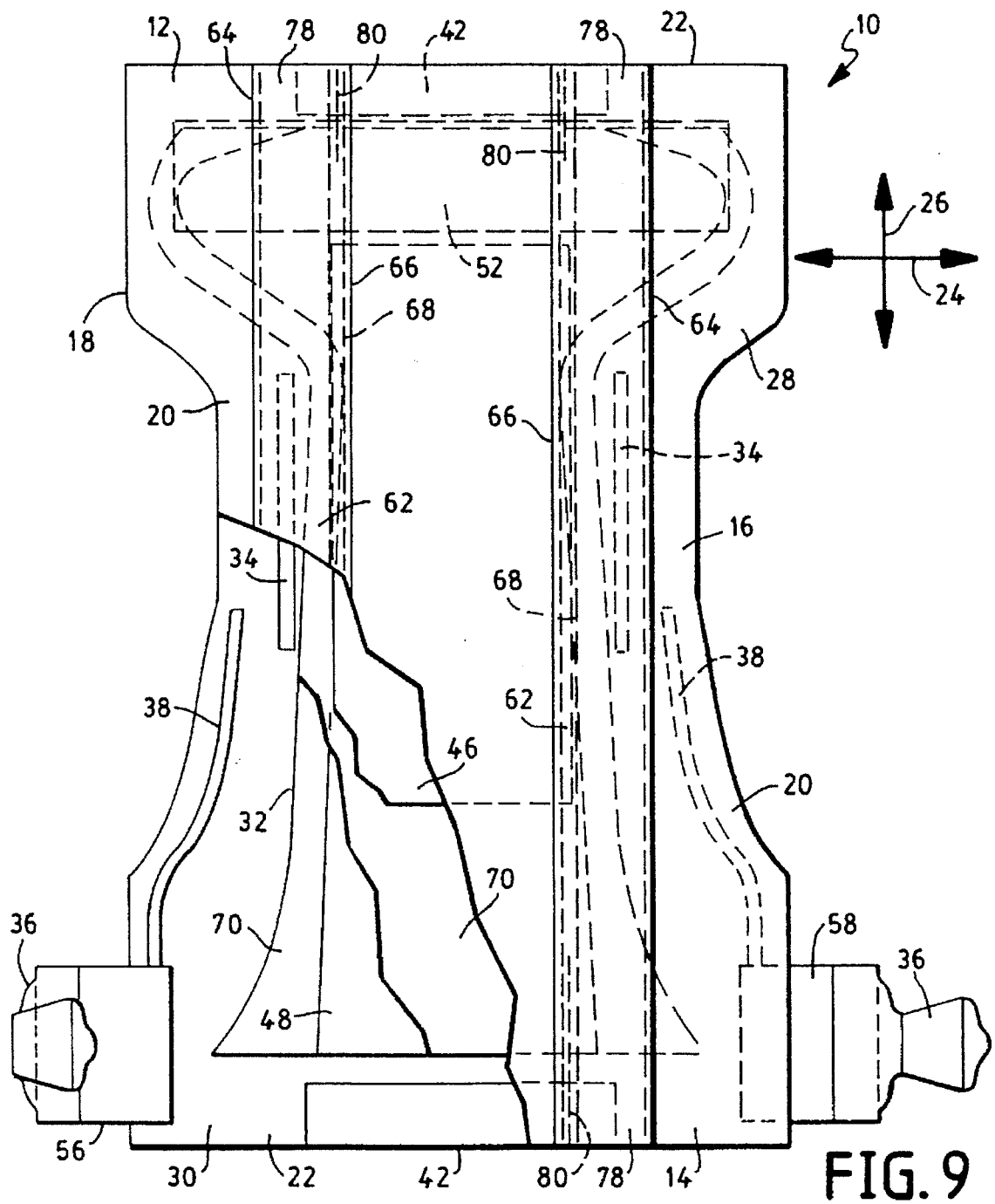
FIG. 9 representatively shows a partially cut-away, top plan view of an article of the invention having a pair of containment flaps wherein each containment flap is attached to the article at a location which is laterally outboard from a corresponding front leg elastic member and is laterally inboard from a corresponding back leg elastic member.

The various configurations of the invention can include elasticized containment flaps 62, as representatively shown in FIGS. 7 through 9. The shown configurations include two containment flaps 62 which are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference in a manner that is consistent herewith. Other configurations of the containment flaps 62 are described in U.S. patent application Ser. No. 208,816 of R. Everett et al., filed Mar. 4, 1994 and entitled ABSORBENT ARTICLE HAVING AN IMPROVED SURGE MANAGEMENT (Attorney docket No. 11,375), the disclosure of which is hereby incorporated by reference in a manner that is consistent herewith.

Such containment flaps can be attached to topsheet layer 28 along length-wise extending fixed regions, such as fixed edges 64, of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In the shown embodiment, for example, the moveable edge of the barrier flap is connected to the flap elastics by partially doubling the flap material back upon itself by a limited amount which is sufficient to enclose flap elastics 68.

With reference to FIGS. 7 through 10, at least a pair of containment or barrier flaps 62 are connected to laterally opposed, longitudinally extending regions of topsheet layer 28, and the connected topsheet regions are located generally adjacent to laterally opposed side edge regions of the medial section of topsheet layer 28. The connected topsheet regions can also be located substantially laterally inboard of the elasticized side margins of the diaper article 10.

The containment flaps may, for example, be constructed of a fibrous material which is similar to the material comprising topsheet 28, or similar to the material comprising surge management portion 46. Other conventional materials, such as polymer films, may also be employed. In other aspects of the invention, barrier flaps 62 are constructed of a material which is permeable to gas, such as ambient air. Alternative configurations of the invention can include barrier flaps which are constructed of a material which is resistant to a passage of aqueous liquid, such as urine, therethrough. For example, barrier flaps 62 may be constructed of a spunbond-meltblown-spunbond (SMS) laminate material. In the illustrated embodiment, for example, the barrier flaps can be constructed of a SMS material having a basis weight of about 0.85 osy (about 26 gsm). The spunbond layers are composed of polypropylene fibers, and the meltblown layer is composed of meltblown polypropylene fibers.

In the various configurations of the invention, such as where the barrier flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated 31 Dec. 1968.

Figure 10:
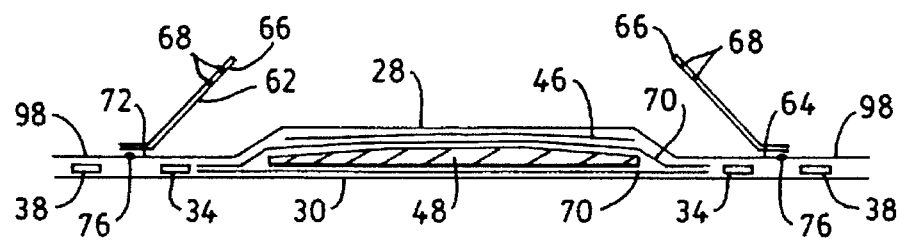
FIG. 10 representatively shows a schematic, expanded, cross-sectional view taken through Section 10—10 of FIG. 9.

With reference to FIGS. 8 and 10, each of the barrier flaps 62 can include a laterally extending base section 72 thereof with at least a portion of the base section attached to the topsheet layer 28 at a topsheet securement section 98, which is located laterally outboard of the retention portion 48 and laterally outboard of the surge management portion 46. The topsheet securement section 98 of topsheet layer 28 can be operably sealed to the backsheet layer 30 to substantially prevent or block a leakage of liquid through the securement section 98. The securement section can be constructed by employing various conventional techniques, such as adhesive bonding, thermal bonding, sonic bonding, stitching, stapling, or the like. The illustrated embodiment, for example, is configured with the topsheet securement section 98 sealed to the backsheet layer 30 with a substantially continuous adhesive bead or strip 76 composed of a pressure-sensitive, hot melt adhesive.

The adhesive strip can advantageously provide a barrier bead which extends generally length-wise of the diaper, and at least a portion of the barrier bead is located in the diaper crotch region 16. The crotch portion of the barrier bead can be constructed to operably bond and substantially seal the corresponding portion of the securement section 98 of topsheet layer 28 to both the barrier flap base section 72 and the backsheet layer 30 by effectively "bleeding" through the topsheet layer 28 to make operable contact with the backsheet layer. When a substantially continuous seal is provided, liquid can be more effectively contained between the two flaps 62. The representative adhesive strip 76 is wiped or otherwise applied onto the appointed section of the flap base 72 at a position which interposes the strip between the terminal side edge of tissue wrap 70 and the leg elastic carrier sheet. Additional pressure can be applied to the adhesive strip area to help assure a desired seal.

At least a portion of the base section can also be attached to the topsheet layer 28 along a topsheet seam section located along the fixed edge 64 of the containment flap. A suitable connecting means, such as a substantially continuous adhesive bead 74, operably secures the fixed barrier flap edge to the topsheet seam section.

With reference to FIG. 9, for example, the representatively shown configuration of each containment flap can include an attached edge region 64 which is located substantially laterally outboard of a corresponding front leg elastic member 34 and substantially laterally inboard of a corresponding back leg elastic member 38. Alternatively, the containment flap attached edge region 64 can be located substantially laterally inboard of a corresponding front leg elastic member 34 and substantially laterally outboard of a corresponding back leg elastic member 38. In an optional configuration of the containment flaps representatively shown in FIG. 7, each of the containment flaps 62 can have an attached edge region 64 connected to the article at a location which is substantially laterally inboard of its corresponding front and back leg elastic members 34 and 38 respectively.

Figure 11:
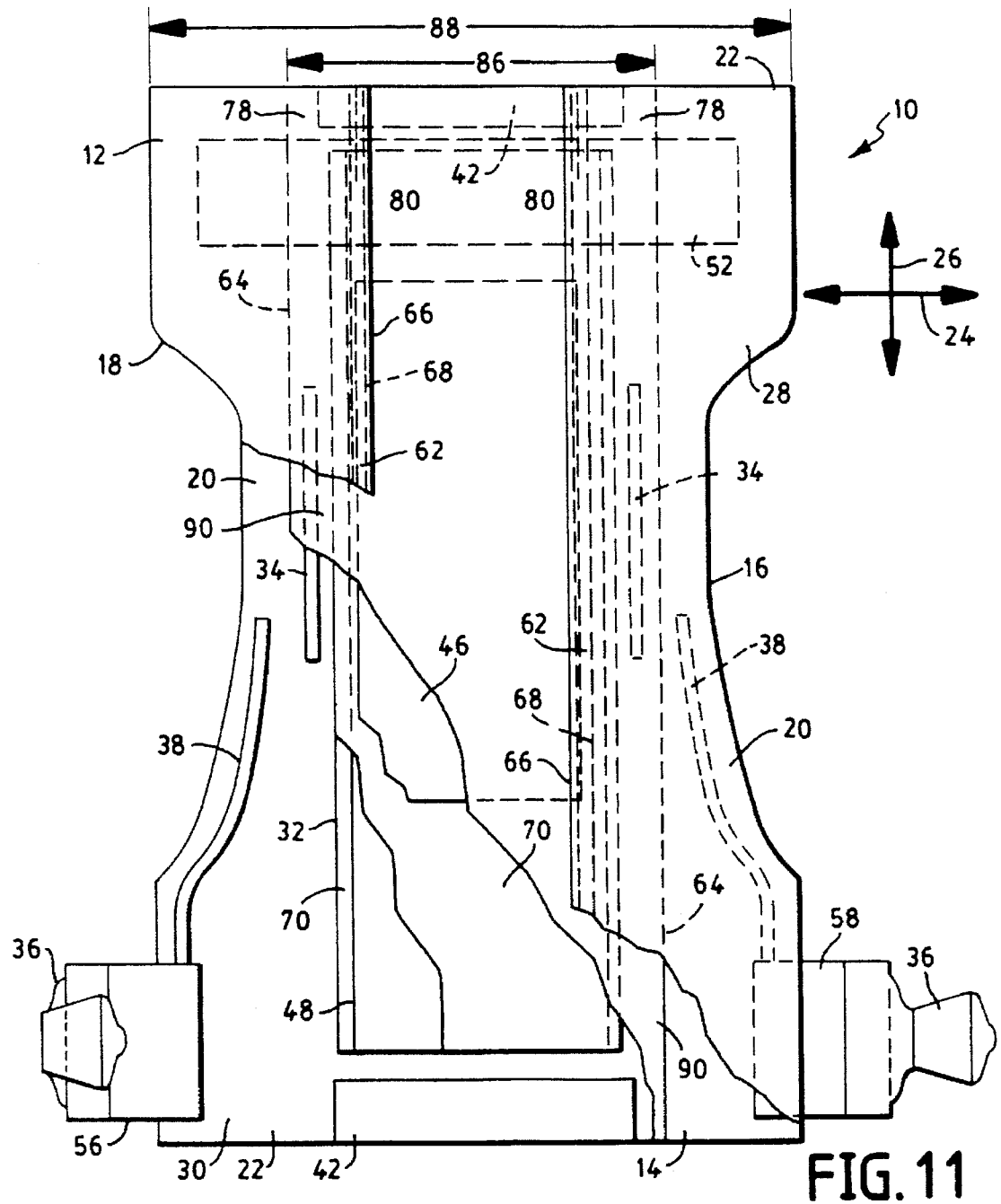
FIG. 11 representatively shows a partially cut-away, top plan view of an article of the invention constructed with a topsheet layer having a lateral width dimension which is narrower than a lateral width dimension of the backsheet layer.
Figure 12:
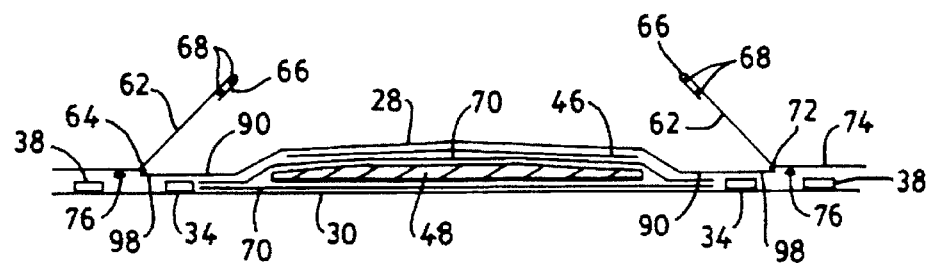
FIG. 12 representatively shows a schematic, expanded, cross-sectional view taken through Section 12—12 of FIG. 11.

With reference to FIGS. 11 and 12, topsheet 28 can have a width dimension 86, and backsheet 30 has a width dimension 88 which is greater than the topsheet width 86. The relatively narrower width topsheet layer 28 has longitudinally extending side edge regions 90. The front leg elastic members 34 are positioned relatively inboard of the topsheet side edge regions 90. Each containment flap 62 includes an extending base section 72 which extends along the longitudinal length of the containment flaps and extends laterally to the terminal side edges of the article. The containment flap base section is laminated to backsheet 30 in the region between the terminal side edges of the article and the topsheet side edge regions 90 with a suitable attaching mechanism. The containment flap can be attached to the topsheet side edge regions 90 along a containment flap seam section 74 employing a suitable securing mechanism. In addition, the containment flap base section 72 can be substantially continuously secured along a barrier bead section 76 which extends longitudinally of the article and is positioned relatively outboard of the front leg elastic members 34 and relatively inboard of the back leg elastic members 38.

Figure 13:
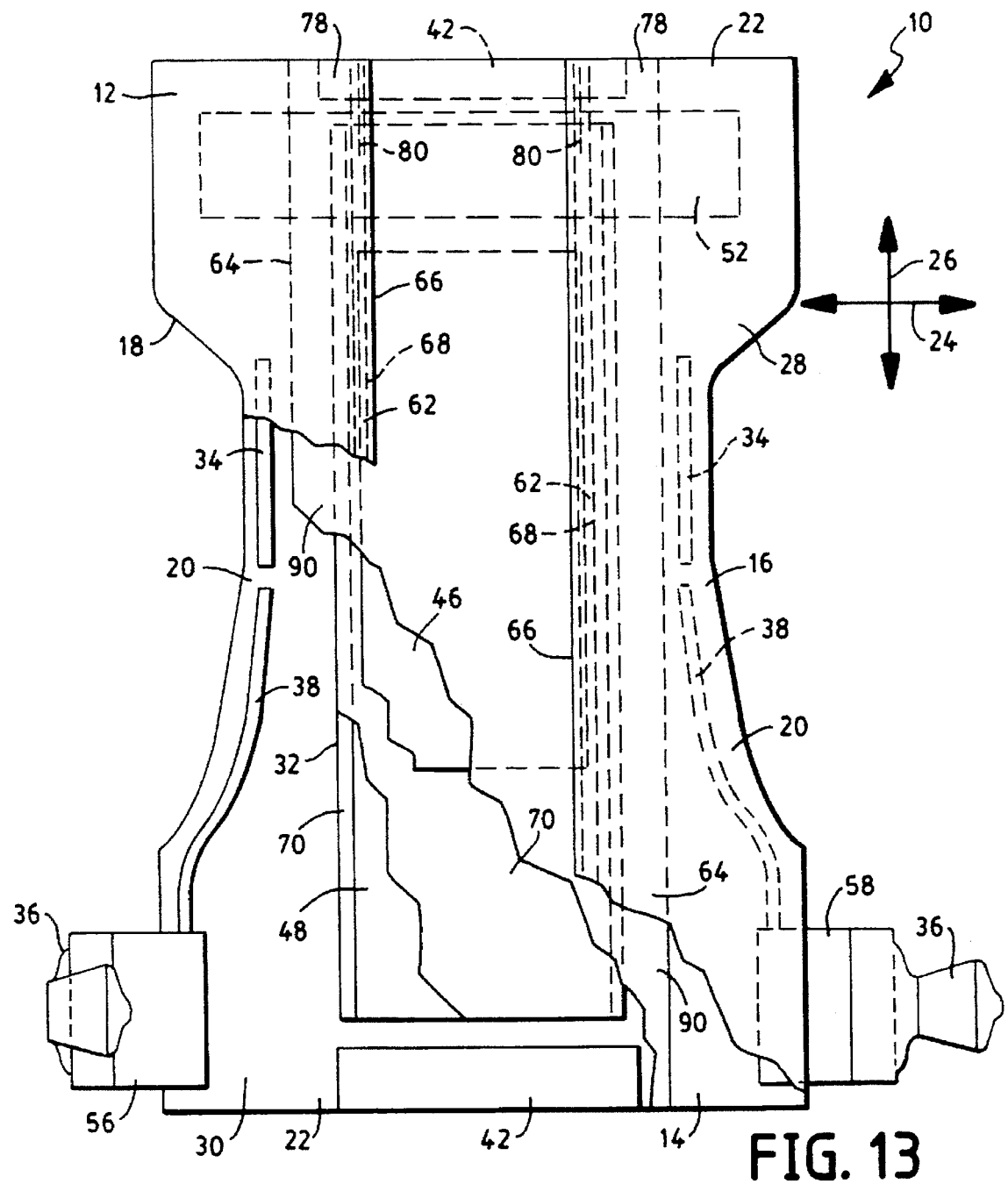
FIG. 13 representatively shows a partially cut-away, top plan view of another article of the invention constructed with a topsheet layer having a lateral width dimension which is narrower than a lateral width dimension of the backsheet layer, wherein the containment flaps attach to the topsheet layer at a location which is laterally inboard from the front and back leg elastic members.
Figure 14:
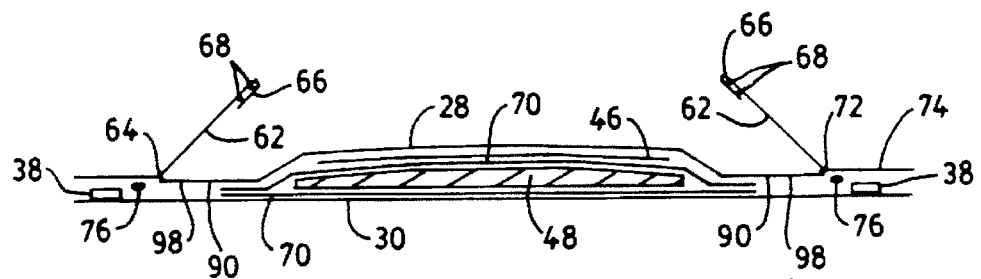
FIG. 14 representatively shows a schematic, expanded, cross-sectional view taken through Section 14—14 of FIG. 13.

With reference to FIGS. 13 and 14, the topsheet width 86 can terminate at a location which is relatively inboard from each of the front and back leg elastic members 34 and 38, respectively. Each of the containment flaps 62 has a base section 72 which extends laterally from its corresponding article side edge to connect with a correspondingly associated side edge region 90 of topsheet 28. Each containment flap includes a seam section 74 which connects to a correspondingly associated topsheet side edge region 90.

Accordingly, the containment flap seam sections are located inboard of each of the front and back leg elastic members 34 and 38, respectively. The containment flap base section 72 can optionally include a barrier attachment section 76 which connects the containment flap base section 72 to backsheet 30 along a substantially continuous longitudinally extending barrier bead section 76.

The various configurations of the containment flaps can also include end attachments 80 which operably hold predetermined longitudinal end sections 78 of the containment flap against the bodyside surface topsheet layer 28. The end attachments 80 are typically restricted and limited to the selected, longitudinally spaced, end sections of the containment flaps. In this configuration, the containment flaps can provide containment pocket structures which can more effectively reduce leakage.

Figure 15:
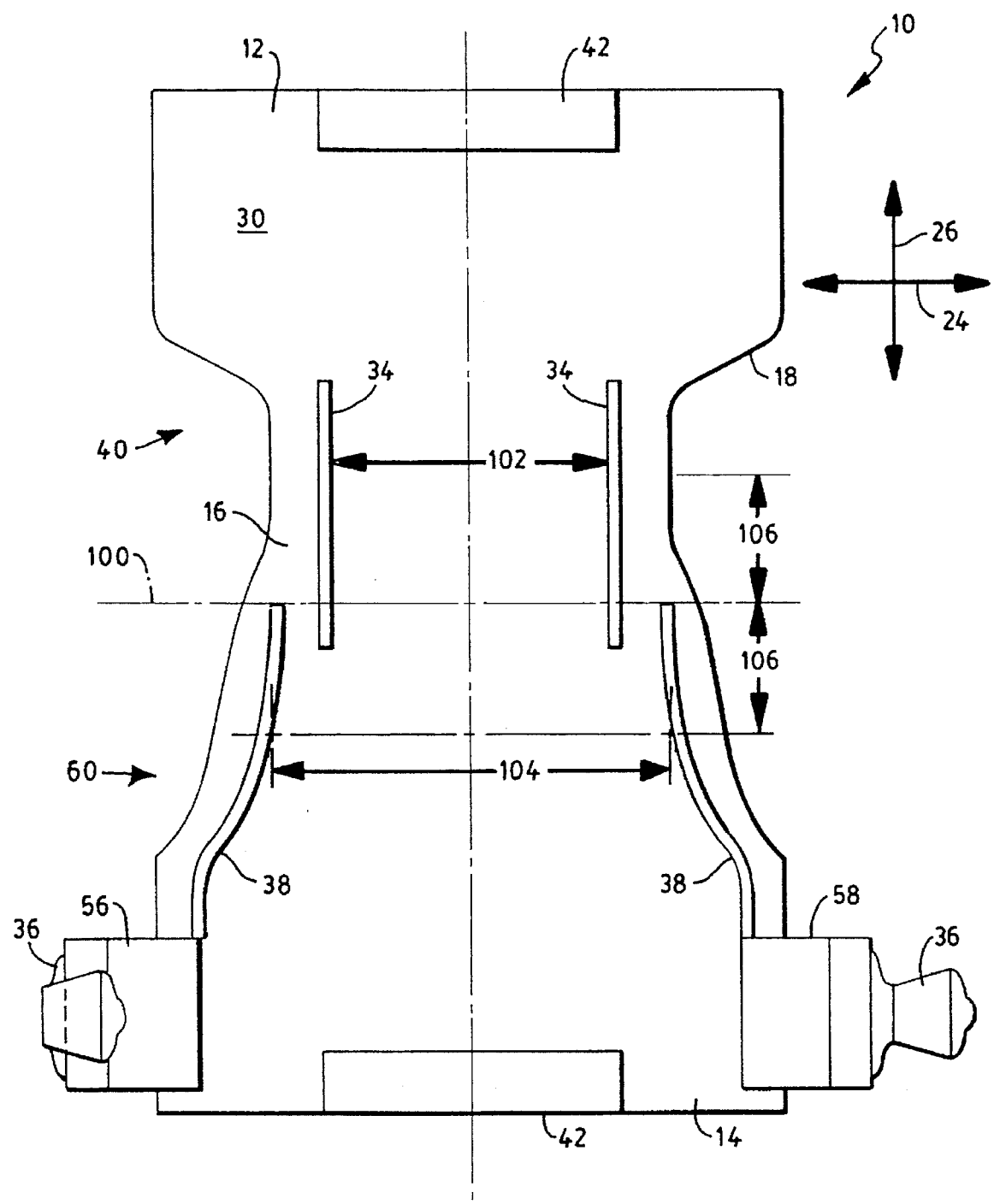
FIG. 15 representatively shows a top plan view of an article of the invention in which the absorbent structure and the components overlying the leg elastics have been removed for the purposes of clarity.

With reference to FIG. 15, the various configurations of the invention can incorporate a distinctive lateral placement ratio (LPR) with respect to a front, cross-directional spacing distance 102 between the front leg elastics located in the laterally opposed side margins 20 of the diaper; and a back, cross-directional spacing distance 104 between the back leg elastics located in the laterally opposed, diaper side margins. Front spacing distance 102 is measured along the diaper cross-direction at a position which is in the front diaper half-section 40 and is at a 2 inch distance 106 away from the transverse centerline 100 (length-wise center), and the 2 inch distance is measured with respect to an extended, flat-out article. Similarly, back spacing distance 104 is measure along the diaper cross-direction at a position which is in the back diaper half-section 60 and is at a two inch distance 106 away from the length-wise center of the extended article. The LPR is determined by dividing the back spacing distance 104 by the front spacing distance 102. The differential spacing of the front leg elastics and back leg elastics can be produced by various constructions or combinations of constructions. For example, the differential spacing can be generated by the amount of lateral offset between a front leg elastic and its corresponding back leg elastic, or by the amount of curvature imparted to either or both of the front and back leg elastics.

In particular aspects of the invention, the LPR is at least about 1.1. Alternatively, the LPR is at least about 1.2, and optionally is at least about 1.3 to provide improved fit. In other aspects of the invention, the LPR is not more than about 10. Alternatively, the LPR is not more than about 5, and optionally is not more than about 3 to provide improved characteristics. The shown embodiment, for example, can have an LPR of about 1.4, and a preferred LPR can be about 2.8. When the LPR is in the desired ranges, the diaper can provide improved fit. The relatively narrower spaced front leg elastics can provide better conformance of the article about the front of the legs of the wearer, and the more widely spaced back elastics can provide improved conformance of the article about the larger, buttock regions of the wearer.

Further improvements to the fit and containment characteristics of the article can be provided by incorporating a differential elasticization between the front leg elastics 34 and the back leg elastics 38. More particularly, the front leg elastics can be configured with a relatively lower elastic tension and/or a relatively lower elastic retraction percentage, as compared to the back leg elastics. For the purposes of the present description, the elastic tension is the tension force exerted by the stretched elastic when the connected, gathered section of the article is extended to its flat-out configuration. The percent retraction is determined by measuring the retracted length of the elastic in the gathered section of the article and measuring the extended length of the elastic when the gathered section is stretched to its flat-out configuration. The percent retraction is then the extended length divided by the retracted length.

In particular aspects of the invention, the elastic tension of the front leg elastics is at least about 25 gm-force. Alternatively, the front leg elastic tension is at least about 35 gm-force, and optionally is at least about 50 gm-force to provide desired benefits. In other aspects of the invention, the elastic tension of the front leg elastics is not more than about 180 gm-force. Alternatively, the front leg elastic tension is not more than about 125 gm-force, and optionally is not more than about 100 gm-force to provide improved performance. Additionally, the percent retraction of the front leg elastics can be at least about 10%. Alternatively, the front percent retraction can be at least about 15%, and optionally can be at least about 20% to provide further benefits. In further aspects, the percent retraction of the front leg elastics can be not more than about 80%. Alternatively, the front percent retraction can be not more than about 70%, and optionally can be not more than about 60% to provide desired performance. In the shown embodiment, for example, the front leg elastic tension can be about 75 gm-force, and the front percent retraction can be about 40%.

With regard to the back leg elastics, the elastic tension of the can be at least about 30 gm-force. Alternatively, the back leg elastic tension can be at least about 50 gm-force, and optionally can be at least about 75 gm-force to provide desired benefits. In other aspects of the invention, the elastic tension of the back leg elastics can be not more than about 210 gm-force. Alternatively, the back leg elastic tension can be not more than about 190 gm-force, and optionally can be not more than about 170 gm-force to provide improved performance. Additionally, the percent retraction of the back leg elastics can be at least about 30%. Alternatively, the back percent retraction can be at least about 40%, and optionally can be at least about 50% to provide further benefits. In further aspects, the percent retraction of the back leg elastics can be not more than about 90%. Alternatively, the back percent retraction can be not more than about 80%, and optionally can be not more than about 70% to provide desired performance. In the shown embodiment, for example, the back leg elastic tension can be about 135 gm-force, and the front percent retraction can be about 60%.

In the various configurations of the invention, the article can comprise side panel members 56 and 58. The side panels are separate members which are operably connected and attached to laterally opposed end regions of the back waistband portion of backsheet 30. The side panels can be composed of a substantially non-elastomeric material, such as polymer films, woven fabrics, nonwoven fabrics or the like, as well as combinations thereof. In particular aspects of the invention, the side panels are composed of a substantially elastomeric material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Mormon, the disclosure of which is hereby incorporated by reference.

Fastening means, such as tape tab fasteners 36, are typically applied to the back waistband region 14 of diaper 10 to provide a mechanism for holding the diaper on the wearer. Tape tab fasteners 36 can be any of those well known in the art, and are typically applied to the corners of diaper 10. For example, adhesive fasteners, mechanical fasteners, hook and loop fasteners, snaps, pins or buckles, may be used alone, or in combination. In the shown configuration, the fasteners are adhesive fasteners, which are constructed to releasably adhere to a landing zone patch 52 attached to the front waistband section of the diaper to provide a refastenable adhesive fastening system. More particularly, the fastener tabs 36 connect to associated, laterally outboard edge regions of the side panels 56 and 58 along an appointed factory-bond region of the tab fasteners. In particular aspects of the invention, the fastener tabs can have a relatively wide user-bond section in combination with a relatively narrower intermediate section. The intermediate section is positioned between the user-bond and factory-bond sections of the fastener tab.

Articles which include non-elastomeric or elastomeric side panels and distinctively configured fasteners are described in U.S. patent application Ser. No. 168,615 of T. Roessler et al., entitled DYNAMIC FITTING DIAPER and filed Dec. 16, 1993 (Attorney docket No. 10,961), the disclosure of which is hereby incorporated herein by reference in a manner that is consistent herewith. The fastening systems can include a stress beam member for distributing the applied stresses over the area of the side panel material, and can include fastening tabs which incorporate a necked down intermediate region in combination with a relatively wider, user-bond section thereof. Techniques for forming the desired fastening systems are described in U.S. patent application Ser. No. 200,593 of T. Roessler et al., entitled METHOD FOR MAKING A FASTENING SYSTEM FOR A DYNAMIC FITTING DIAPER and filed Feb. 23, 1994 (Attorney docket No. 11,186), the disclosure of which is hereby incorporated herein by reference in a manner that is consistent herewith.

Having thus described the invention in rather full detail, it will be readily apparent that various changes and modifications can be made without departing from the spirit of the invention. All of such changes and modifications are contemplated as being within the scope of the invention, as defined by the subjoined claims.

We claim:

1. An absorbent article having a lateral width, a longitudinal length, longitudinally extending side margins, a front waistband portion, a back waistband portion and an intermediate portion which interconnects said front and back waistband portions, said article comprising:
   a backsheet layer;
   an absorbent retention portion superposed on said backsheet layer;
   a liquid permeable topsheet layer superposed on said retention portion to sandwich said retention portion between said topsheet layer and said backsheet layer; and
   elasticizing means for forming elasticized gathers at leg opening portions of said article; said elasticizing means including
   a front set of laterally opposed, longitudinally extending front leg elastic members located in said article side margins beyond said in at least said intermediate and front portions of said article; and
   a back set of laterally opposed, longitudinally extending back leg elastic members which are located in said article side margins in at least said intermediate portion of said article, said back elastic members arranged asymmetrically with respect to said article length with a selected offset toward said back waistband portion of said article, each of said back elastic members arranged to have a longitudinal overlap with its corresponding front elastic members at a location within its corresponding article side margin and laterally outboard of said retention portion, and each back elastic member arranged laterally spaced from its corresponding front elastic member along the entire longitudinal overlap.

2. The absorbent article as recited in claim 1, wherein said front leg elastic members and said back leg elastic members are arranged in a mutually, partially-overlapping relation within said article side margins at said location laterally outboard of said retention portion.

3. The absorbent article as recited in claim 2, wherein said back leg elastics are located outboard of said front elastic members.

4. The absorbent article as recited in claim 2, wherein said back leg elastic members are arranged in a substantially linear configuration and are located outboard of said front elastic members.

5. The absorbent article as recited in claim 2, wherein said front leg elastic members have a relatively lower elastic tension as compared to an elastic tension of said back leg elastic members.

6. The absorbent article as recited in claim 5, wherein said front leg elastic members have a relatively lower percent retraction as compared to a percent retraction of said back leg elastic members.

7. The absorbent article as recited in claim 2, further comprising a pair of laterally opposed, longitudinally extending containment flaps, each containment flap having an attached edge region and a movable edge region, said attached edge region located substantially laterally outboard of a corresponding front leg elastic member and substantially laterally inboard of a corresponding back leg elastic member.

8. The absorbent article as recited in claim 2, further comprising a pair of laterally opposed, longitudinally extending containment flaps, each containment flap having an attached edge region and a movable edge region, said attached edge region located substantially laterally inboard of a corresponding front leg elastic member and substantially laterally outboard of a corresponding back leg elastic member.

9. The absorbent article as recited in claim 1, wherein said back leg elastic members are arranged in a substantially curvilinear configuration.

10. The absorbent article as recited in claim 9, wherein said back leg elastic members are located outboard of said front leg elastic members.

11. The absorbent article as recited in claim 10, wherein said front leg elastic members are arranged in a substantially curvilinear configuration.

12. The absorbent article as recited in claim 1, wherein at least about 55% of said front leg elastic members are located in a front half-section of said article.

13. The absorbent article as recited in claim 12, wherein at least about 55% of said back leg elastic members are located in a back half-section of said article.

14. The absorbent article as recited in claim 1, wherein each of said front leg elastic members is laterally spaced from a corresponding back leg elastic member by a distance which is not less than about 0.5 cm.

15. The absorbent article as recited in claim 1, wherein said front leg elastic members and said back leg elastic members provide a lateral placement ratio of at least about 1.1.

16. The absorbent article as recited in claim 1, wherein each of said front leg elastic members is arranged in a substantially linear configuration.

17. The absorbent article as recited in claim 1, further comprising a pair of laterally opposed, longitudinally extending containment flaps, each containment flap having an attached edge region and a movable edge region, said attached edge region located substantially laterally inboard of corresponding front and back leg elastic members.

18. The absorbent article as recited in claim 1, wherein at least one of said front and back leg elastic members includes a plurality of separate generally longitudinally extending, elastomeric strands.

19. An absorbent article having a lateral width, a longitudinal length, longitudinally extending side margins, a front waistband portion, a back waistband portion and an intermediate portion which interconnects said front and back waistband portions, said article comprising:
   a backsheet layer;
   an absorbent retention portion superposed on said backsheet layer;
   a liquid permeable topsheet layer superposed on said retention portion to sandwich said retention portion between said topsheet layer and said backsheet layer;
   elasticizing means for forming elasticized gathers at leg opening portions of said article; said elasticizing means including
      a front set of laterally opposed, longitudinally extending front leg elastic members located in said article side margins in at least said intermediate and front portions of said article; and
      a back set of laterally opposed, longitudinally extending back leg elastic members which are located in said article side margins in at least said intermediate portion of said article, said back elastic members arranged asymmetrically with respect to said article length with a selected offset toward said back waistband portion of said article, and each of said back elastic members arranged to have a longitudinal overlap with its corresponding front elastic member at a location which is within said article side margins and laterally outboard of said retention portion,
      wherein each of said front leg elastic members and its corresponding back leg elastic members are arranged in a mutually, partially-overlapping relation at said location within said article side margins; and
   further comprising a pair of laterally opposed, longitudinally extending containment flaps, each containment flap having an attached edge region and a movable edge region, said attached edge region located substantially laterally outboard of a corresponding front leg elastic member and substantially laterally inboard of a corresponding back leg elastic member.

20. An absorbent article having a lateral width, a longitudinal length, longitudinally extending side margins, a front waistband portion, a back waistband portion and an intermediate portion which interconnects said front and back waistband portions, said article comprising:
   a backsheet layer;
   an absorbent retention portion superposed on said backsheet layer;
   a liquid permeable topsheet layer superposed on said retention portion to sandwich said retention portion between said topsheet layer and said backsheet layer;
   elasticizing means for forming elasticized gathers at leg opening portions of said article; said elasticizing means including
      a front set of laterally opposed, longitudinally extending front leg elastic members located in said article side margins in at least said intermediate and front portions of said article; and
      a back set of laterally opposed, longitudinally extending back leg elastic members which are located in said article side margins in at least said intermediate portion of said article, said back elastic members arranged asymmetrically with respect to said article length with a selected offset toward said back waistband portion of said article and each of said back elastic members arranged to have a longitudinal overlap with its corresponding front elastic member at a location which is within said article side margins and laterally outboard of said retention portion,
      wherein each of said front leg elastic members and its corresponding back leg elastic members are arranged in a mutually, partially-overlapping relation at said location within said article side margins; and
   further comprising a pair of laterally opposed, longitudinally extending containment flaps, each containment flap having an attached edge region and a movable edge region, said attached edge region located substantially laterally inboard of a corresponding front leg elastic member and substantially laterally outboard of a corresponding back leg elastic member.

21. An absorbent article having a lateral width, a longitudinal length, longitudinally extending side margins, a front waistband portion, a back waistband portion and an intermediate portion which interconnects said front and back waistband portions, said article comprising:
   a backsheet layer;
   an absorbent retention portion superposed on said backsheet layer;
   a liquid permeable topsheet layer superposed on said retention portion to sandwich said retention portion between said topsheet layer and said backsheet layer;
   elasticizing means for forming elasticized gathers at leg opening portions of said article; said elasticizing means including
      a front set of laterally opposed, longitudinally extending front leg elastic members located in said article side margins in at least said intermediate and front portions of said article; and
      a back set of laterally opposed, longitudinally extending back leg elastic members which are located in said article side margins in at least said intermediate portion of said article, said back elastic members arranged asymmetrically with respect to said article length with a selected offset toward said back waistband portion of said article, and each of said back elastic members arranged to have a longitudinal overlap with its corresponding front elastic member at a location which is within said article side margins and laterally outboard of said retention portion,
      wherein each of said front leg elastic members and its corresponding back leg elastic members are arranged in a mutually, partially-overlapping relation at said location within said article side margins; and
   further comprising a pair of laterally opposed, longitudinally extending containment flaps, each containment flap having an attached edge region and a movable edge region, said attached edge region located substantially laterally inboard of corresponding front and back leg elastic members.

22. An absorbent article having a lateral width, a longitudinal length, longitudinally extending side margins, a front waistband portion, a back waistband portion and an intermediate portion which interconnects said front and back waistband portions, said article comprising:

a backsheet layer;

an absorbent retention portion superposed on said backsheet layer;

a liquid permeable topsheet layer superposed on said retention portion to sandwich said retention portion between said topsheet layer and said backsheet layer; and elasticizing means for forming elasticized gathers at leg opening portions of said article; said elasticizing means including a front set of laterally opposed, longitudinally extending front leg elastic members located in said article side margins in at least said intermediate and front portions of said article; and a back set of laterally opposed, longitudinally extending back leg elastic members which are located in said article side margins in at least said intermediate portion of said article, said back elastic members arranged asymmetrically with respect to said article length with a selected offset toward said back waistband portion of said article, and each of said back elastic members arranged to have a longitudinal overlap with its corresponding front elastic member at a location which is within said article side margins and laterally outboard of said retention portion, wherein each of said front leg elastic members and its corresponding back leg elastic members are arranged in a mutually, partially-overlapping relation at said location within said article side margins; and wherein said front leg elastic members have a relatively lower elastic tension as compared to an elastic tension of said back leg elastic members.

23. An absorbent article having a lateral width, a longitudinal length, longitudinally extending side margins, a front waistband portion, a back waistband portion and an intermediate portion which interconnects said front and back waistband portions, said article comprising:

a backsheet layer;

an absorbent retention portion superposed on said backsheet layer;

a liquid permeable topsheet layer superposed on said retention portion to sandwich said retention portion between said topsheet layer and said backsheet layer; and elasticizing means for forming elasticized gathers at leg opening portions of said article; said elasticizing means including a front set of laterally opposed, longitudinally extending front leg elastic members located in said article side margins in at least said intermediate and front portions of said article; and a back set of laterally opposed, longitudinally extending back leg elastic members which are located in said article side margins in at least said intermediate portion of said article, said back elastic members arranged asymmetrically with respect to said article length with a selected offset toward said back waistband portion of said article, and each of said back elastic members arranged to have a longitudinal overlap with its corresponding front elastic member at a location which is within said article side margins and laterally outboard of said retention portion, wherein each of said front leg elastic members and its corresponding back leg elastic members are arranged in a mutually, partially-overlapping relation at said location within said article side margins, and wherein said front leg elastic members have a relatively lower percent retraction as compared to a percent retraction of said back leg elastic members.

* * * * *